Figure 1:
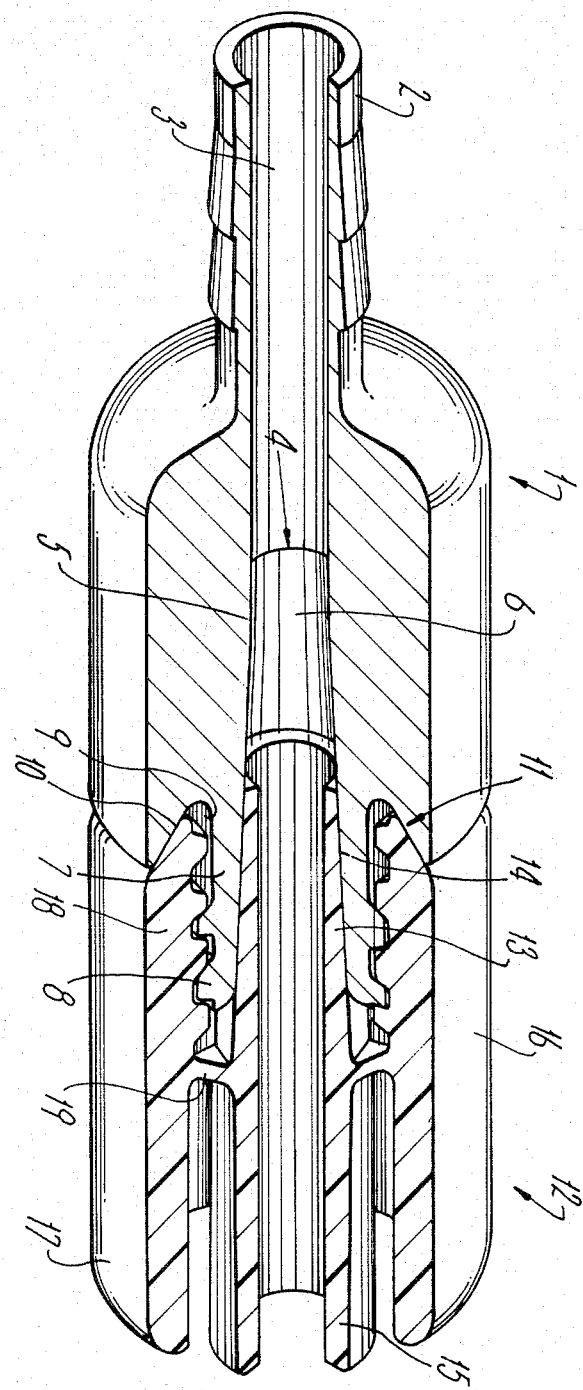

United States Patent [19]

Donnan et al.

[11] Patent Number: 4,526,572
[45] Date of Patent: Jul. 2, 1985

[54] MEDICAL CONNECTOR

[75] Inventors: Jeremy F. Donnan; David A. Reed, both of Nottinghamshire, England

[73] Assignee: The Boots Company PLC, Nottingham, England

[21] Appl. No.: 509,124

[22] Filed: Jun. 29, 1983

[30] Foreign Application Priority Data

Jun. 30, 1982 [GB] United Kingdom ............... 8218860

[51] Int. Cl.³ .................... A61M 5/00; F16L 27/10
[52] U.S. Cl. ................................. 604/29; 604/283
[58] Field of Search .................. 604/29, 283, 905; 285/331, 371, 398, 332

[56] References Cited

U.S. PATENT DOCUMENTS

| | | | |
|---|---|---|---|
| 3,659,881 | 5/1972 | Tinsley et al. | 285/371 |
| 3,986,731 | 10/1976 | De Hoff | 285/371 |
| 4,076,285 | 2/1978 | Martinez . | |
| 4,133,312 | 1/1979 | Burd | 285/332 |
| 4,209,013 | 6/1980 | Alexander et al. . | |
| 4,242,310 | 12/1980 | Greff et al. . | |
| 4,294,250 | 10/1981 | Dennehey | 604/905 |
| 4,334,551 | 6/1982 | Pfister . | |
| 4,340,052 | 7/1982 | Dennehey et al. . | |
| 4,346,703 | 8/1982 | Dennehey et al. . | |
| 4,353,367 | 10/1982 | Hunter et al. . | |
| 4,354,490 | 10/1982 | Rogers . | |
| 4,369,779 | 1/1983 | Spencer . | |
| 4,403,992 | 9/1983 | Bertellini et al. . | |
| 4,405,312 | 9/1983 | Gross et al. . | |
| 4,457,749 | 7/1984 | Bellotti et al. | 604/29 |

FOREIGN PATENT DOCUMENTS

| | | |
|---|---|---|
| 893623 | 10/1982 | Belgium . |
| 1105959 | 7/1981 | Canada . |
| 28198 | 5/1981 | European Pat. Off. . |
| 62148 | 10/1982 | European Pat. Off. . |
| 3048892 | 7/1982 | Fed. Rep. of Germany . |
| 2486803 | 1/1982 | France . |
| 2506162 | 11/1982 | France . |
| WO82/04187 | 12/1982 | PCT Int'l Appl. . |
| WO83/00447 | 2/1983 | PCT Int'l Appl. . |
| 1193759 | 6/1970 | United Kingdom . |
| 2024974 | 1/1980 | United Kingdom . |
| 1582914 | 1/1981 | United Kingdom . |
| 2060399 | 5/1981 | United Kingdom . |
| 2089921 | 6/1982 | United Kingdom . |

Primary Examiner—C. Fred Rosenbaum
Assistant Examiner—Michelle N. Lester
Attorney, Agent, or Firm—Lawrence Rosen

[57] ABSTRACT

A connector for medical tubing comprises two interengaging parts (1, 12). As one part is rotated relative to the other, screw-threads cause a tapered projection (13) to mate with a flared bore (6) to provide a fluid-tight seal. Further relative rotation causes the outer bevelled edge of the outer wall (16) of one of the parts to move further forward to sealingly engage the sloping wall (10) of the other part. The projection (13) and outer wall (16) are connected by a flexible membrane 19 to permit this further forward movement. The connector is particularly suited for use in continuous ambulatory peritoneal dialysis.

5 Claims, 6 Drawing Figures

MEDICAL CONNECTOR

The present invention relates to connectors for medical tubing and particularly relates to connectors for use in medical apparatus intended for continuous ambulatory peritoneal dialysis (CAPD).

CAPD is a medical treatment in which a dialysis solution is introduced into the peritoneal cavity of the patient, allowed to remain there for several hours and then drained from the patient's peritoneal cavity with this process being repeated on a substantially continuous basis. The usual manner of achieving this type of dialysis involves connecting a dialysis solution container to a catheter connected to the patient's peritoneal cavity, unclamping the tubing between the dialysis solution container and the patient's peritoneal cavity so as to allow the dialysis solution to flow from the container to the peritoneal cavity, thereafter reclamping the tubing, allowing the dialysis solution to remain within the patient's peritoneal cavity for several hours, unclamping the tubing and draining the solution from the patient's peritoneal cavity back to the dialysis solution container, disconnecting the dialysis solution container from the catheter tube and connecting to the catheter tube a fresh dialysis solution container, and repeating the above cycle. It is important that the connector which connects a solution container to the catheter is easy to use, provides a secure connection and does not introduce the possibility of infection entering the peritoneal cavity of the patient.

The present invention provides a connector for medical tubing comprising (a) a first part which has means for releasably connecting the first part to a second part of the connector and which has a central projection having a flared axial bore and a contact zone around the base of the central projection, and (b) a second part which has means which are engagable with the connecting means on the first part for releasably connecting the first and second parts, a tapered axial projection which fits inside the flared bore of the first part to provide a fluid-tight seal when the parts are interconnected and an outer wall which surrounds the tapered projection and which is connected to the tapered projection by a flexible membrane which allows relative axial movement between the outer wall and the tapered projection, when the tapered projection of the second part is in sealing contact with the flared bore of the first part, from a position in which the forwardmost end of the outer wall of the second part is spaced from the contact zone to a position in which the forwardmost end of the outer wall of the second part is in sealing contact with the contact zone.

Conveniently the means for releasably connecting the two parts comprise an outwardly extending screw-thread around the central projection on the first part and a corresponding inwardly extending screw-thread on the inner surface of the outer wall of the second part.

The contact zone on the first part may comprise an annular groove which may be defined by the outer wall of the central projection and by the inner wall of an annular projection extending from the first part around, and coaxially with, the central projection. The inner wall of the annular projection may slope so as to make contact with a corresponding bevel on the outermost end of the outer wall of the second part to provide the sealing contact when the parts are interconnected.

When the connector of the present invention is used in apparatus for continuous ambulatory peritoneal dialysis the first part of the connector is permanently connected to a catheter leading to the peritoneal cavity of the patient and the second part is connected to tubing leading to a container of dialysis fluid. Conveniently the first part of the connector is manufactured from a metal such as medical grade stainless steel or titanium and the second part of the connector is manufactured (e.g. by injection moulding techniques) from a medically acceptable thermoplastic material.

Figure 2:
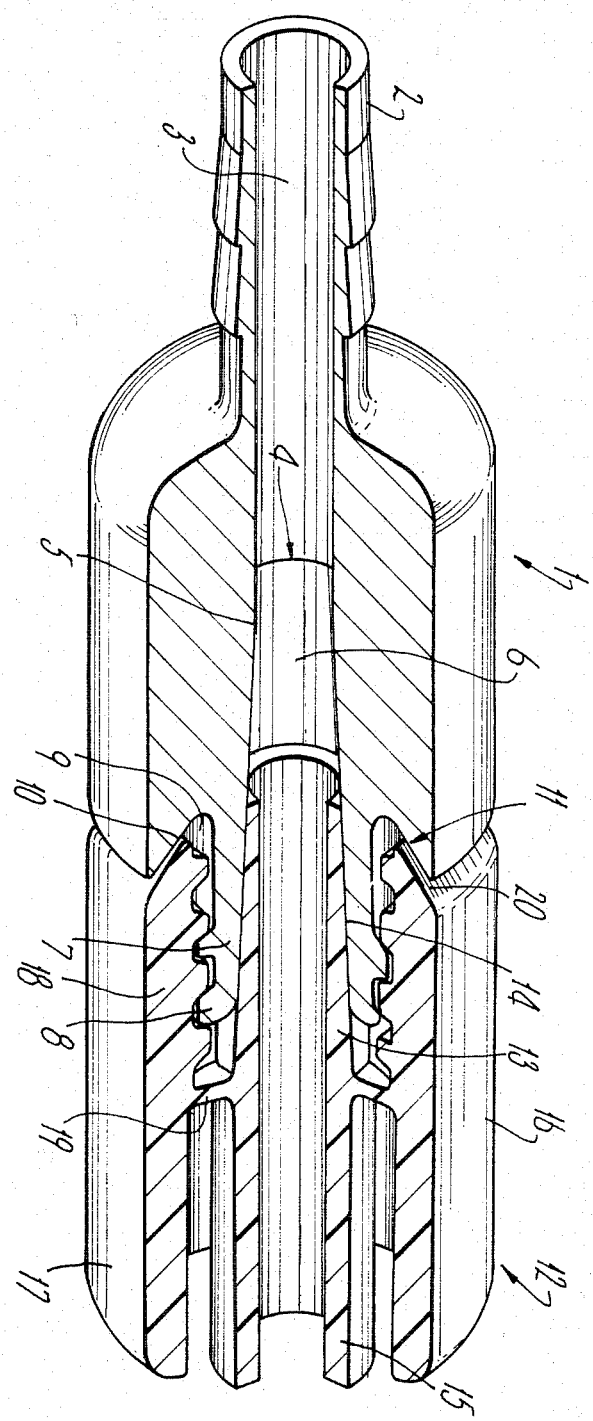
Figure 3A:
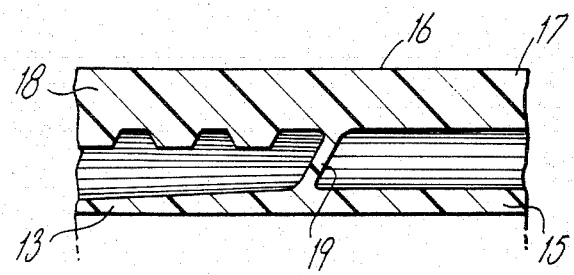
Figure 3B:
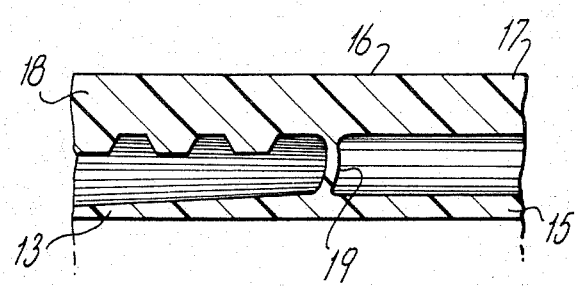

The invention will be illustrated by the following description of an embodiment thereof. The description has reference to the accompanying drawings in which:

FIG. 1 is a partially cut-away isometric view of a connector embodying the present invention, FIG. 2 is a view similar to FIG. 1 but showing the two parts of the connector partially interconnected, FIGS. 3(a) and 3(b) are diagrammatic cross-sectional views of a part of the connector shown in FIGS. 1 and 2, and FIGS. 4(a) and 4(b) are diagrammatic cross-sectional views similar to FIGS. 3(a) and 3(b) but showing an alternative embodiment.

The connector comprises a first part 1 which is connected in use to a catheter (not shown) which leads to the peritoneal cavity of the patient. The catheter is attached to a nozzle 2 extending from the first part 1. The first part 1 has an axial bore 3 which is of uniform cross-section as it passes through the nozzle 2 and that part of the body of the first part adjacent the nozzle 2 but which increases from the point 4 and becomes progressively larger in diameter. Conveniently the amount of the increase is such that the frusto-conical surface 5 of the flared portion 6 of the bore 4 deviates from the axis of the bore 3 by 6%. A projection 7 having outwardly extending screw-threads 8 extends from the end of the first part opposite the nozzle 2. The flared portion 6 of the bore 3 passes through the projection 7. Around the base of the projection 7 is an annular groove 9 defined by the projection 7 and the sloping wall 10 of an annular projection 11 extending from the periphery of the body of the first part. The annular projection 11 is coaxial with and surrounds the projection 7.

Conveniently the first part 1 is manufactured from a metal which is inert to the dialysis fluid used in CAPD. Suitable metals include medical grade stainless steels and titanium.

The connector also comprises a second part 12 which may be manufactured from a medically-acceptable thermoplastic material for example by injection moulding. The second part comprises a tapered projection 13 which has a frusto-conically tapered outer surface 14 which is capable of being received in and of forming a fluid-tight seal with the flared portion 6 of the bore 3 of the first part 1. A uniform bore passes axially through the tapered projection 13 and through a tubular projection 15 to which the tubing from a dialysis container (not shown) may be attached. Around the projections 13, 15 is an annular outer wall 16 which has a first section 17 surrounding, and of substantially the same height as, the tubular projection 15 and a second section 18 which surrounds the tapered projection 13 but which is of less height than the tapered projection. The inside surface of the second section 18 of the outer wall 16 is screw-threaded to co-operate with the screw-threads 8 on the projection 7 of the first part of the connector. The outer end of the second section 18 is bevelled so that it can sealingly contact the sloping wall 10 of the first part of the connector when the two parts are interengaged as shown in FIG. 1. The outer wall 16 and the central body which is made up of the projections 13, 15 are connected by a thin flexible membrane 19 which extends from generally the middle of the inside surface of the outer wall 16 to that point on the central body where the projections 13, 15 meet. The flexible membrane 19 permits the central body and the outer wall to move axially relative to one another. When the second part of the connector is only partially interconnected to the first part as shown in FIG. 2, the membrane urges the outer wall 16 towards the right as shown in the drawings. As the two parts are interconnected, the outer wall is moved relative to the central body to ensure satisfactory sealing as will be described hereinafter. This is important as it ensures that, when the two parts are fully interconnected (a) the frusto-conical surface 5 of the flared portion 6 and the tapered outer surface 14 of the projection 13 form a fluid-tight seal and (b) the sloping wall 10 of the annular projection 11 and the bevelled end of the second section 18 of the outer wall 16 are in sealing contact to minimise the ingress of undesirable contaminants.

The flexibility of the membrane 19 ensures that as the screw-threads on the projection 7 and on the inside surface of the second section 18 of the outer wall 16 are interengaged by relative rotation of the two parts, the two parts move together so that the tapered projection 13 on the second part forms a fluid-tight seal against the flared portion 6 of the bore of the first part. This position is illustrated in FIG. 2 in which the reference numeral 20 indicates the gap between the sloping wall 10 and the bevelled end of the second section 18. Further relative rotation of the two parts then causes the outer wall 16 to be moved axially relative to the projection 13 until the bevelled end of the second section contacts and seals against the sloping wall 10 on the first part of the connector. The inclusion of the flexible membrane allows this to be done. If the membrane had been rigid there would have been no possibility of relative axial movement between the central body and the outer wall 16 and even very small deviations from the ideal dimensions of the two parts of the connector would have caused one or other of the two seals required to be unsatisfactory. The present invention ensures that satisfactory sealing can occur when there is some deviation from the ideal dimensions as there must be even in the best-controlled mass production techniques. As the outer wall 15 moves relative to the projection 13 as described above the flexible membrane is put under tension. This tension acts to hold the projection in a sealing position inside the bore of the first part of the connector and to minimise the chance of the sealing contact being broken.

Figure 4A:
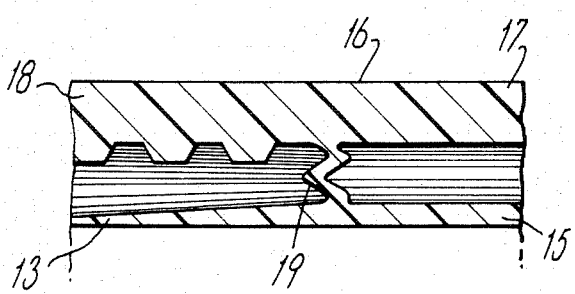
Figure 4B:
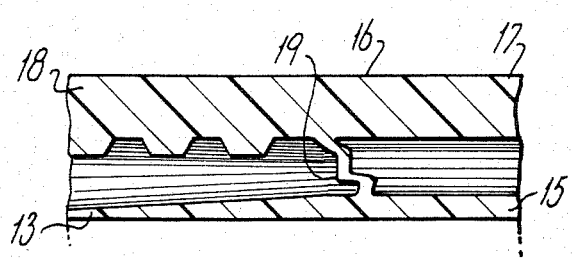

FIGS. 3(a) and 3(b) show in diagrammatic cross-section the membrane in the positions which it adopts in FIG. 2 and in FIG. 1 respectively. FIGS. 4(a) and 4(b) are similar to FIGS. 3(a) and 3(b) but show an alternative embodiment of the membrane 19 in which the membrane is folded in a concertina manner. This concertina folding allows a larger amount of relative axial movement between the outer wall 16 and the tapered projection 13 than is possible with the embodiment shown in FIGS. 1 to 3.

We claim:

1. A connector for medical tubing comprising
(a) a first part which has means for releasably connecting the first part to a second part of the connector and which has a central projection having a flared axial bore and a contact zone around the base of the central projection, and
(b) a second part which has means which are engagable with the connecting means on the first part for releasably connecting the first and second parts, a tapered axial projection which fits inside the flared bore of the first part to provide a fluid-tight seal when the parts are interconnected and an outer wall which surrounds the tapered projection and which is connected to the tapered projection by a flexible membrane which allows relative axial movement between the outer wall and the tapered projection, when the tapered projection of the second part is in sealing contact with the flared bore of the first part, from a position in which the forwardmost end of the outer wall of the second part is spaced from the contact zone to a position in which the forwardmost end of the outer wall of the second part is in sealing contact with the contact zone.

2. A connector as claimed in claim 1 in which the means for releasably connecting the two parts comprise an outwardly extending screw-thread around the central projection on the first part and a corresponding inwardly extending screw-thread on the inner surface of the outer wall of the second part.

3. A connector as claimed in claim 1 or claim 2 in which the contact zone on the first part comprises an annular groove defined by the outer wall of the central projection and by the inner wall of an annular projection extending from the first part around, and coaxially with, the central projection.

4. A connector as claimed in claim 3 in which the inner wall of the annular projection slopes so as to be engageable with a corresponding bevel on the forwardmost end of the outer wall of the second part to provide the sealing contact when the parts are interconnected.

5. Apparatus for continuous ambulatory peritoneal dialysis comprising a catheter leading to the peritoneal cavity of the patient and tubing leading to a container for dialysis fluid, said catheter and tubing being connected by a connector as claimed in any one of claims 1 to 4 with the first part of the connector being connected to the catheter and the second part of the connector being connected to the tubing.

* * * * *